Nov. 17, 1936. C. C. MAYHEW Plant Pat. 205
BRONZE CHRYSANTHEMUM
Filed Feb. 7, 1936
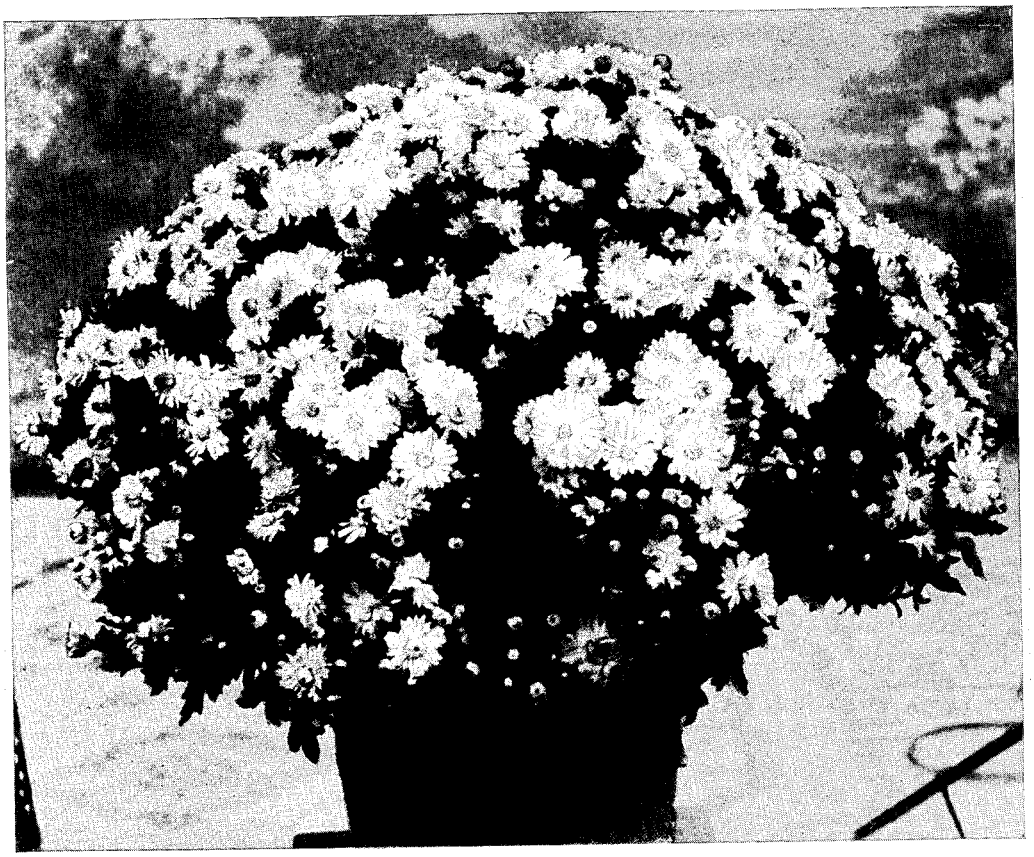
Inventor
Clarence C. Mayhew
By Robert Robb
Attorney Patented Nov. 17, 1936

Plant Pat. 205

UNITED STATES PATENT OFFICE

205

BRONZE CHRYSANTHEMUM

Clarence C. Mayhew, Sherman, Tex., assignor to
Texas Nursery Company, Sherman, Tex.

Application February 7, 1936, Serial No. 62,831

1 Claim. (Cl. 47—60)

My present discovery relates to chrysanthemums of the polyanthous type or class, wherein the plants are many flowered. The blossoms of my new variety, similarly to those of the azalea, grow in such a manner as to give a spheroidal or mound-like appearance to the blooming plant, which presents flowers all over its outer surface.

My new variety of chrysanthemum is a sport originating from a variety of chrysanthemum identical with the latter in all characteristics of form, habit, and growth, though distinguishing therefrom in regard to the color of its blossoms. The color of the blooms of my new variety is bronze in general appearance, while the variety from which it sported has blooms which are pink in color.

My new variety of chrysanthemum, and the variety from which it sported, both differ from other varieties of chrysanthemums in regard to their blooming period. The former bloom from two to three weeks earlier than the latter in the region of Texas.

My new variety ordinarily shows blooms from about the first of May until the first of December in this region, reaching the peak of its blooming period from about the middle of October to the middle of November.

My new variety of chrysanthemum is dwarf in type, attaining a height of fifteen to eighteen inches in the region of Texas. It is suitable for growing out of doors, and is especially desirable for garden decoration.

It is emphasized that the essential feature of distinction of my new variety over the variety from which it sported lies in the bronze color of the flower of the former.

My new variety of chrysanthemum has been found to hold its distinguishing characteristics through succeeding generations by means of asexual reproduction, propagation being carried on from cuttings.

The following is a detailed description of my new variety of chrysanthemum:—

*Plant.*—Mound-like in form.

*Flower.*—Many to a stem, of rounded form.

*Stem.*—Strong, rather short.

*Quality of bloom.*—Abundant—outdoors.

*Continuity.*—Continuous.

*Fragrance.*—Moderate, spicy.

*Bloom.*—When fully open is medium, 1½ to 2 inches across.

*Petalage.*—Double, arranged regularly.

*Color.*—Compared with Ridgway's Chart.

*Buds.*—Tones of Morocco and Brazil red (Plate I) and burnt sienna (Plate II).

*Flowers.*—Opening xanthine orange (Plate III) blending to a glow of lemon yellow (Plate IV) at base of petals, with center petals tipped with Morocco red (Plate I) and burnt sienna (Plate II). The flower matures to light cadmium (Plate IV) with tints of Mars orange and burnt sienna (Plate II) on outer petals. All stages on the plant at one time.

Description of flowers made from newly opened flowers grown outdoors.

*Foliage.*—Moderate, dark green.

*Growth.*—Dwarf, spreading, much branched.

I claim:—

A new and distinct variety of chrysanthemum plant as herein shown and described, characterized by its polyanthous and mound-like habit of growth, its early blooming habit, and the bronze color of its flower.

CLARENCE C. MAYHEW.